US008066761B2

(12) United States Patent
Caro et al.

(10) Patent No.: US 8,066,761 B2
(45) Date of Patent: Nov. 29, 2011

(54) STENTING METHOD FOR BLOOD VESSELS (75) Inventors: Colin Gerald Caro, London (GB);
Denis Joseph Doorly, London (GB);
Mary Anne McLean, Rickmansworth (GB)

(73) Assignee: Veryan Medical Limited, Oxford (GB)

( * ) Notice: Subject to any disclaimer, the term of this patent is extended or adjusted under 35 U.S.C. 154(b) by 597 days.

(21) Appl. No.: 12/006,437

(22) Filed: Jan. 2, 2008

(65) Prior Publication Data
US 2008/0109067 A1 May 8, 2008

Related U.S. Application Data (62) Division of application No. 09/857,012, filed as application No. PCT/GB99/03999 on Nov. 30, 1999, now Pat. No. 7,326,240.

(30) Foreign Application Priority Data

Nov. 30, 1998 (GB) .................................. 9826254.6

(51) Int. Cl.
*A61F 2/06* (2006.01)
(52) U.S. Cl. ...................... 623/1.15; 623/1.16; 623/1.22
(58) Field of Classification Search ................. 623/1.22, 623/1.15–1.16, 1.19, 1.3–1.31; 606/153
See application file for complete search history.

(56) References Cited

U.S. PATENT DOCUMENTS

| 4,629,458 | A |   | 12/1986 | Pinchuk |   |
|---|---|---|---|---|---|
| 4,886,062 | A |   | 12/1989 | Wiktor |   |
| 5,015,253 | A |   | 5/1991 | MacGregor |   |
| 5,104,404 | A |   | 4/1992 | Wolff |   |
| 5,108,417 | A |   | 4/1992 | Sawyer |   |
| 5,354,308 | A |   | 10/1994 | Simon et al. |   |
| 5,443,498 | A |   | 8/1995 | Fontaine |   |
| 5,579,767 | A |   | 12/1996 | Prince |   |
| 5,670,161 | A | * | 9/1997 | Healy et al. | ................. 623/1.42 |
| 5,697,971 | A |   | 12/1997 | Fischell et al. |   |
| 5,879,381 | A | * | 3/1999 | Moriuchi et al. | ............ 623/1.16 |
| 5,882,335 | A |   | 3/1999 | Leone et al. |   |
| 5,993,483 | A |   | 11/1999 | Gianotti |   |
| 6,015,387 | A |   | 1/2000 | Schwartz et al. |   |
| 6,039,754 | A | * | 3/2000 | Caro | ......................... 623/1.35 |
| 6,071,305 | A |   | 6/2000 | Brown et al. |   |
| 6,156,062 | A |   | 12/2000 | McGuinness |   |
| 6,206,911 | B1 | * | 3/2001 | Milo | .......................... 623/1.15 |

(Continued)

FOREIGN PATENT DOCUMENTS

EP    0615769    9/1994

(Continued)

*Primary Examiner* — Paul Prebilic
(74) *Attorney, Agent, or Firm* — Fay Sharpe LLP (57) ABSTRACT

A method of imposing a shape on an intact blood vessel other than a graft includes inserting a stent in the vessel. The stent includes a supporting portion which internally supports an interior wall of the vessel. The supporting portion includes a hollow tube, the walls of which have openings therein so that the interior wall of the vessel is exposed via the openings to fluid flow along the vessel. A central axis of the hollow tube forms a non-planar three dimensional at least partially helical shape. The hollow tube imposes the three-dimensional at least partially helical shape on the central axis of the vessel, inducing a swirling fluid flow within the stent supported part of the vessel.

18 Claims, 5 Drawing Sheets

U.S. PATENT DOCUMENTS

| | | |
|---|---|---|
| 6,206,914 B1 * | 3/2001 | Soykan et al. ............... 623/1.42 |
| 6,221,101 B1 | 4/2001 | Harris et al. |
| 6,425,915 B1 | 7/2002 | Khosravi et al. |
| 6,554,856 B1 | 4/2003 | Doorly et al. |
| 6,569,191 B1 | 5/2003 | Hogan |
| 7,722,663 B1 * | 5/2010 | Austin ..................... 623/1.22 |

FOREIGN PATENT DOCUMENTS

| | | | |
|---|---|---|---|
| GB | 2344053 A | * | 5/2000 |
| WO | WO 92/03107 | | 3/1992 |
| WO | WO 9509585 | | 4/1995 |
| WO | WO 9626682 | | 9/1996 |
| WO | WO 98/53764 | | 12/1998 |

* cited by examiner

STENTING METHOD FOR BLOOD VESSELS

This application is a division of U.S. application Ser. No. 09/857,012 which was filed on Sep. 14, 2001, and is now U.S. Pat. No. 7,326,240. That application is the entry into the National Phase in the United States of International Application Serial No. PCT/GB99/03999 filed on 30 Nov. 1999.

This invention is concerned with stents for supporting parts of blood vessels. More particularly it is concerned with stents as in-situ supporting devices for arteries and veins within the vascular system. The term 'artery' and 'vein' in the singular or plural, refers to the vein or artery or a part thereof but excludes any parts thereof which is a graft or which has been removed to serve as a graft.

Stents are known devices used in surgery especially in vascular surgery for providing physical support to blood vessels i.e. they can be used to help prevent kinking/occlusion of blood vessels such as veins or arteries and to prevent their collapse after dilatation or other treatment to maintain their patency.

It has been proposed that the flow pattern in arteries including the swirling pattern induced by their non-planar curvature operates to inhibit the development of vascular diseases such as thrombosis, atherosclerosis and intimal hyperplasia.

We have now devised an apparatus and technique for establishing and/or maintaining physiological curvature, including non-planar curvature within blocked, constricted or otherwise flow-restricted blood vessels such as arteries or veins as defined above.

By maintaining physiological curvature, which may include non-planar curvature in the blood vessels, favourable blood flow velocity patterns can be achieved often through generation therein of 'swirl' flow.

Failures in such vessels through thrombosis, atherosclerosis, intimal hyperplasia or other diseases leading to blockage or due to kinking or collapse, can be significantly reduced.

According to this invention there is provided a stent for supporting part of a blood vessel, such as part of an intact vein or artery within the vasculature, which stent includes a supporting portion around which or within which part of that blood vessel can be placed so that the stent internally or externally supports that part and the supporting portion of the stent is of a shape and/or orientation whereby flow within the vessel is caused to follow a physiologically appropriate curve which may be non-planar.

The supporting portion of the stent may be fabricated to incorporate means to increase the ability of the stent to sustain displacement due to bending and torsion so that it may more readily accommodate (i) a non-planar curved form; and/or (ii) it may be pre-formed to provide an appropriate geometry to sustain a more favourable flow in the selected vessel after insertion, and/or (iii) a geometric arrangement of the junction between the stent and branching vessel e.g. artery whereby the tangent vector from the centreline of the stent intersects the centreline of the host vessel by consequence of a symmetric disposition of the stent with respect to the host vessel.

The stent may be of generally hollow tubular shape with three dimensional curvature. The stent is particularly preferred for use as an in-situ support internally within or externally around arteries and veins.

The stent may take the form of a series of linked members forming a tubular frame e.g. an open lattice generally tubular framework with discrete openings at each end thereof. Alternatively it may take the form of series of curved rings joined together.

A stent may be passed through the interior section of a blood vessel, which stent then provides support for that part of the blood vessel through which it passes and preferably imparts thereby to the vessel a geometry which includes non-planar curvature i.e. the vessel part supported by the stent can assume and maintain curvature which is non-linear. Part of the supported vessel in such embodiments thereby acquires a geometry which can be regarded as a part-helical or helicoidal curve even if the physical extent of the supported vessel is less than one complete turn of a helix e.g. less than ½ or less than ¼ of such a turn.

A practical embodiment of a non-planar internal stent of type (ii) is one fabricated to adopt an appropriately helicoidal, helical, part helicoidal, or part-helical form, to provide the required support for the blood vessel after its insertion.

In order that the invention may be illustrated, more easily understood and readily carried into effect by one skilled in this art, reference will now be made to the accompanying drawings of preferred embodiments by way of non-limiting example only, and in which.

Figure 1A:
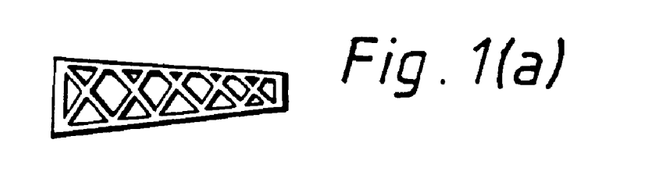
FIGS. 1a to c depict an embodiment of a stent shaped to conform the blood vessel in non-planar curvature at a site where it is deployed.
Figure 1B:
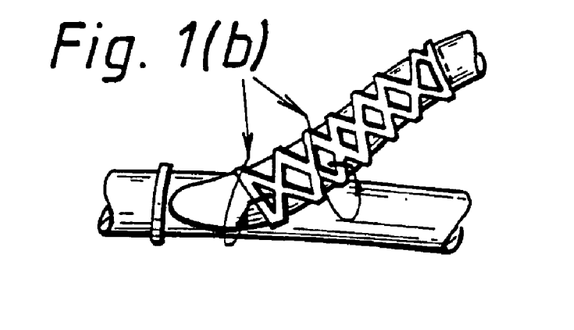
Figure 1C:
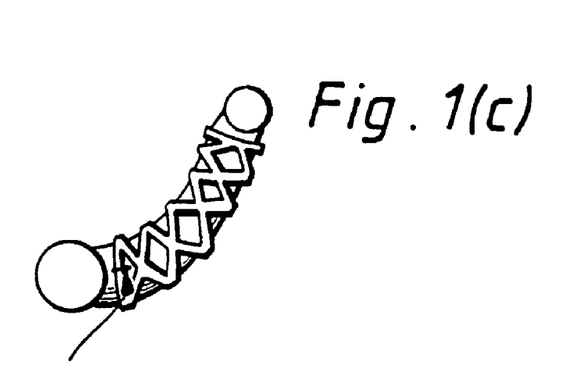

Referring to FIGS. 1a to c of the drawings, the device shown may be fabricated from a thermosettable material, in the form of a hollow tube, the walls of which contain numerous openings so that the interior of the artery is not fully shielded.

In particular, FIG. 1(a) shows the stent before thermosetting, whereas FIGS. 1(b) and (c) indicate possible configurations whereby prior thermosetting has rendered this stent to adopt the shape of a partially coiled, non-planar curve.

The stent is then inserted within the artery to ensure the geometrical configuration of the artery to a predetermined form in the locality of the stent.

The stent may be of constant diameter, or tapered, as in FIG. 1(a) to accommodate the common practice of deploying a stent in the vicinity of the junction of the artery with a parent or daughter artery. The stent may be fixed to the artery by sutures (shown arrowed) or to avoid trauma to the vessel, may be attached to a clip ring placed about the vessel.

The restraining action of the stent may be graduated, by mechanically "tapering" the rigidity of the material: for example, at either end, material may be removed or the rigidity reduced by cuttings. An internally locatable stent is also provided which corresponds to the external stent just described, however such a stent is inserted into the interior of the vessel part rather than being placed exterior to the vessel.

Although intended for the cardiovascular system, embodiments of such stents could be incorporated elsewhere—e.g. in the gastrointestinal system, bile duct, genitourinary system for the "active stent", this might for example be deployed with treatment of incontinence.

Figure 2:
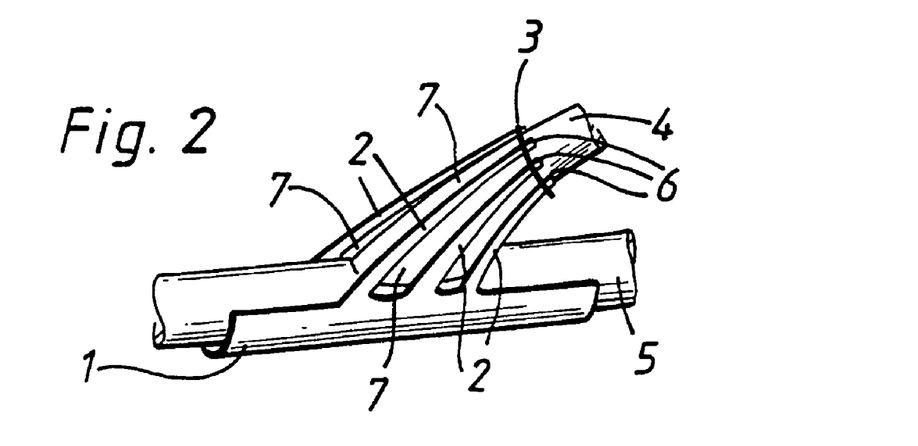
FIG. 2 shows an alternative embodiment of a stent.

Referring to FIG. 2 the non-planarity of the vessel 4 is attained by supporting it with an external stent 1, 2 which comprises a longitudinal part section 1 of a cylinder, fabricated of a suitable porous biocompatible material, which may be of straight or curved section, to support that part of the artery 5 in the region of the stent, and integral with part section 1, or attached securely thereto are a plurality of elongate external support members 2, which are fabricated to define an internal region 7 of appropriate non-planar geometry.

The ends 6 of the support members 2 may be secured in situ by surgical thread (not shown) or by a fastening ring 3. The stented vessel 4 is located within that internal region 7.

Figure 3:
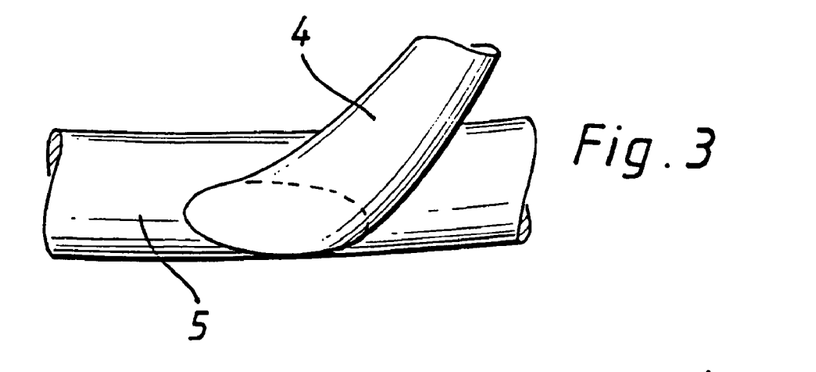
FIG. 3 shows a configuration of an artery with a stent deployed therein.
Figure 3A:
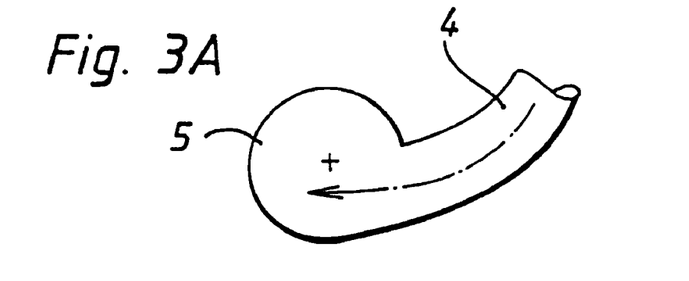
FIG. 3a is a side view of the FIG. 3 arrangement.

FIGS. 3 and 3a depict a non-planar configuration of stent and artery wherein a stent (artery 5, stent 4) having a non-planar curve is surgically attached offset to the central portion of the artery 5 in that it is at least partly tangential to the artery, see the direction of flow arrow in FIG. 3a.

Figure 4:
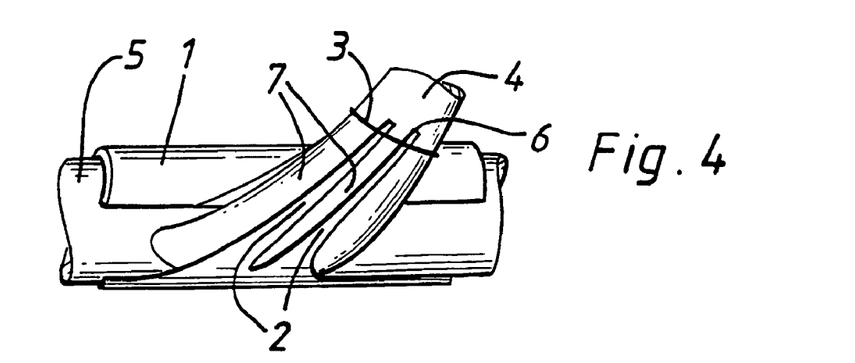
FIG. 4 shows one suitably shaped stent adapted to establish and maintain non-planar curvature in an arterial part (i.e. part of a whole artery) as shown in FIGS. 3 and 3a, FIG. 4a is a side view of the FIG. 4 stent-supported artery.
Figure 4A:
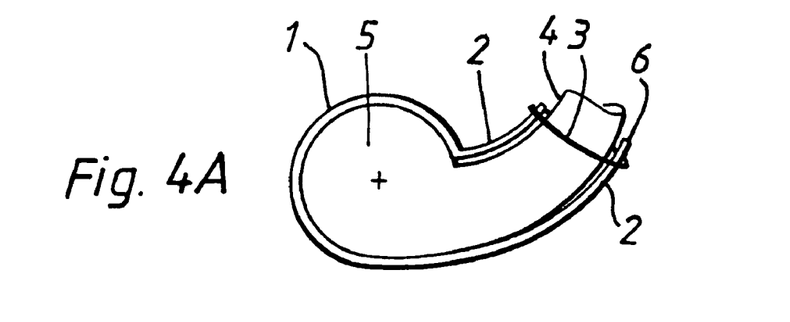

The external stent (1,2) of FIG. 2 can be modified to support and maintain the non-planar curvature of the artery in the FIGS. 3/3a arrangements, by for example the structure as depicted in FIGS. 4/4a. FIGS. 4 and 4a have reference numerals which correspond with those used in FIG. 2 described above.

Figure 5:
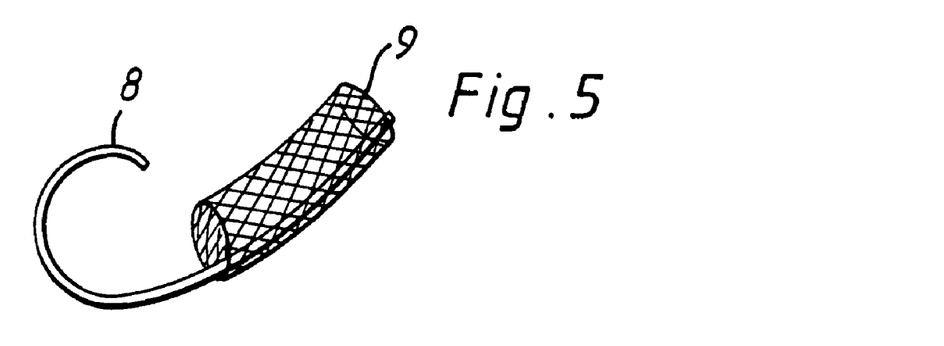
FIG. 5 is an alternative embodiment of an internal stent based on a clip of e.g. shape memory alloy.

As shown in FIG. 5 an internal stent for establishing and/or maintaining non-planar curvature of a vessel part comprises a clip 8 which is part coiled or at least part helical of shape memory alloy, affixed to a cylindrical wire mesh 9. This is an embodiment of a torsionally flexible stent.

Figure 6A:
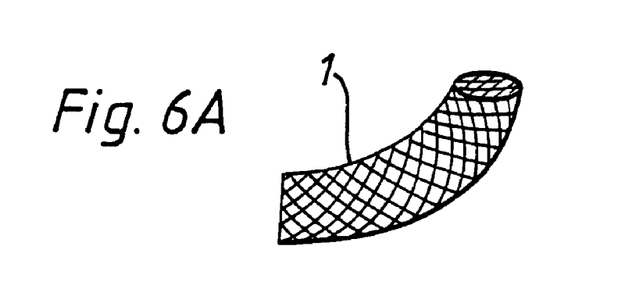
FIGS. 6a and 6b show a part-helical internal stent.
Figures 6B, 6C:
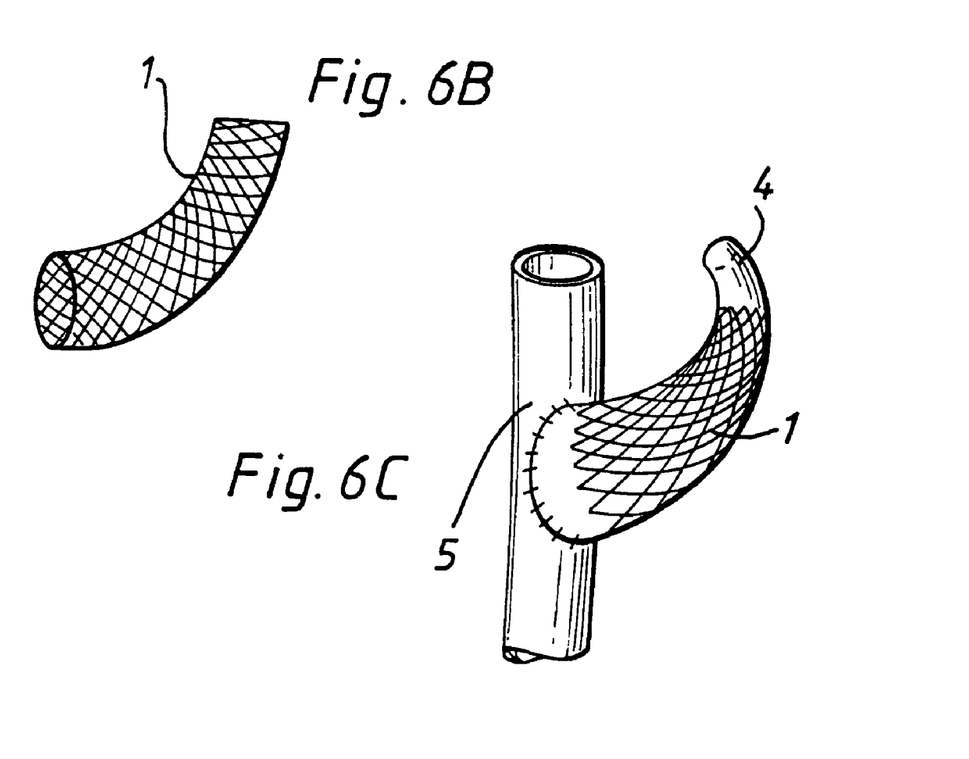
FIG. 6c shows the stent of FIGS. 6a/6b internally supporting an arterial part.

FIGS. 6A and 6B show an alternative embodiment of an internal stent, in which the stent 1 is fabricated from a linked wire mesh of part helical form. The material used is preferably a shape memory alloy to facilitate insertion of the stent. FIG. 6C shows the stent located in the vessel post insertion. The stent 4 surgically attached to artery 5 has been shown 'transparent' for purposes of illustration, to show the internally located, part helical wire mesh stent in-situ.

Figure 7A:
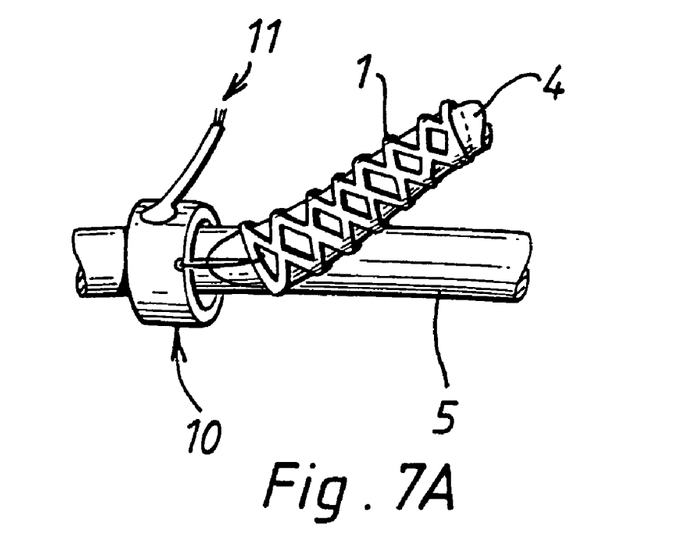
FIG. 7a shows an externally located stent for an artery and a sensor for transmitting flow or other data.
Figure 7B:
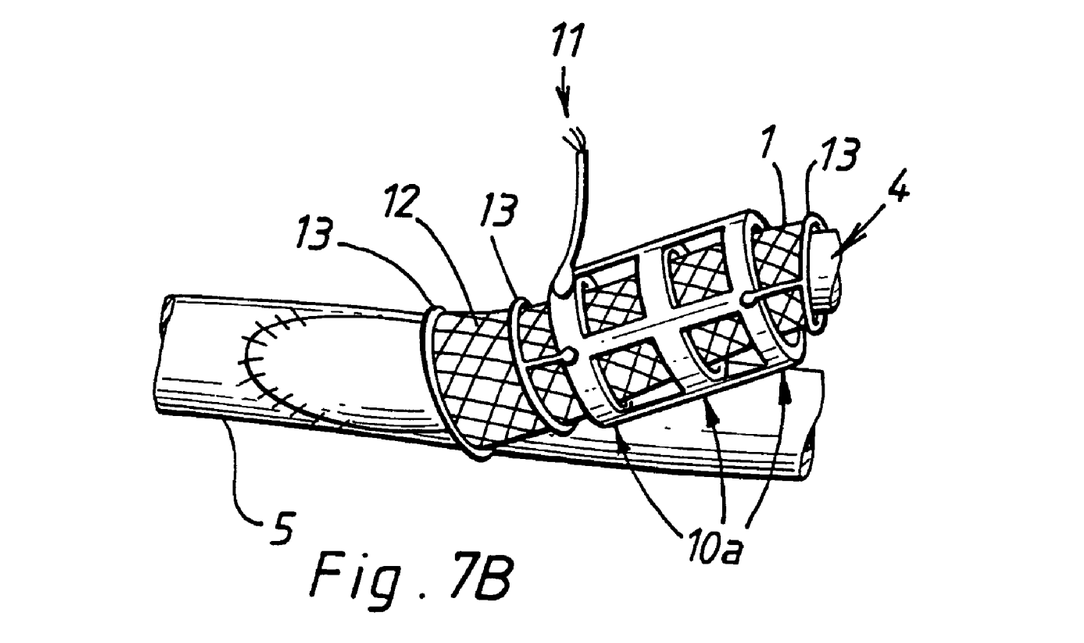
FIG. 7b shows a similar arrangement to FIG. 7a but wherein the sensor is located within the supported arterial part.

Referring to FIGS. 7A and 7B, either internal or external stents may incorporate devices which assist in monitoring the condition of either the graft or the host vessel or both.

In one possible embodiment shown in FIG. 7A, an external stent 1 incorporates a sensor portion 10 for monitoring the condition of the host artery. The sensor portion is a ring placed over the host artery 5, attached to the tubular stent 1 placed over the graft. The sensor and stent may be secured together by means of clips or threads during the operation to insert the graft. The sensor 10 may incorporate one or several ultrasound probes, or it may comprise a coil for use with magnetic resonance imaging. The sensor portion may be electrically connected by leads 11, only partly shown, to a remote module or modules (not shown) which incorporate the required power supply, signal detection and recording devices for data capture and transmission. Some or all of the modules to which the sensor is connected may be implanted within the body of the person receiving the graft, and incorporate appropriate means such as telemetry for transcutaneous data monitoring.

In a still further embodiment, shown in FIG. 7B, an external stent 1 comprises a fabric or porous structure 12 attached to several outer supporting members having the external appearance of linked rings or discs 13. For a portion of the stent, these outer members incorporate a sensor device 10a or series of sensors such as miniature radio frequency and/or gradient coils for magnetic resonance imaging, or ultrasound transducers. The power supply for the sensors, excitation and data monitoring may be as in the FIG. 7A embodiment. Electrical wires 11 connect the sensor device 10a to the appropriate remote module or modules (not shown).

In another embodiment of an internal or external stent the sensor may incorporate a means to detect certain chemical markers which are indicative of the condition of the flow and/or arteries. It may also contain a means whereby a supply of pharmacological agent may be administered in situ, for example by being connected to an implanted supply of drugs which are caused to be delivered by appropriate implanted machinery.

In other embodiments of an internal or external stent, the sensory action of the stent may derive from the construction of some or all of the supporting members which form the stent. In one such embodiment, the sensory action derives from a coil or coils of an electrically conducting material wound around the perimeter of the stent or interspersed at intervals along the stent which coil or coils may be excited by extracorporeal magnetic and/or electromagnetic fields, and the signal from the stent detected by magnetic coupling with an external detecting coil.

Loss of patency of stents remains a serious problem. The principal pathology at later times is intimal hyperplasia and important sites of its occurrence are apparently immediately upstream and downstream of stents. Most attention appears to have focused on compliance mismatch (arterial distensibility greatly exceeds stent distensibility) as underlying this distribution. However, because stents are effectively straight cylinders and arteries curve three dimensionally, compliance mismatch is also likely to be associated with local distortion of arterial geometry and hence distortion of the flowfield, with implications for vessel biology and pathology.

We propose ex vivo studies of stent-induced distortion of the geometry and flowfield in arteries. Stents will be deployed at a few selected sites of non-planar curvature in physiologically pressurized animal arteries and epoxy resin casts will be made of the stented vessels. Geometric data obtained by MRI from the casts, together with a range of assumed physiological flows, will enable detailed determination of the local flowfield including the distribution of wall shear stress by computational (CFD) simulations. In some instances moulds of the epoxy resin casts will be perfused and the flowfield, measured by MRI, will provide a check on the CFD simulations.

As a step towards remedying the problem of stent-induced distortion of the geometry and flowfield in arteries, we propose the deployment of appropriately pre-shaped stents, obtained by exploiting the shape-memory properties of nitinol. After their deployment the local geometry and flowfield will be studied using the same methods as adopted for control stents. The generation of swirling flows and a reduction of the geometric and flowfield distortion would encourage further deployment of pre-shaped shape-memory stents and/or on the engineering of stents less liable to distort the local geometry and flowfield.

The principal questions that need to be addressed are:
(1) How is the geometry of an artery which is naturally curved in three dimensions altered by the insertion of a stent, which restricts the ability of the artery to maintain its curvature?
(2) What are the consequences of this modification in the local geometry for the flowfield within the stent and immediately adjacent to it?
(3) What geometric form should a stented portion of artery adopt in order to obtain as uniform a distribution of wall shear stress within the stent and immediately adjacent to the stent as possible?

The local flow pattern in blood vessels (including wall shear) markedly influences their biology and, it appears, the development of vascular disease.

For example, atherosclerosis appears to develop preferentially at locations in arteries where the wall shear is on average low and/or there are large oscillations of wall shear. Furthermore, the preferred region for the occurrence of intimal hyperplasia at end-to-side arterial bypass grafts appears to be where wall shear is low, there is flow separation, and/or there are large oscillations of wall shear during the cardiac cycle. Increase of blood flow (assumed to imply increase of wall shear) decreases the severity of intimal hyperplasia (or causes the regression of pre-existing disease). However, a very large increase of wall shear in small diameter grafts is associated with low patency rates, seemingly because of thrombosis. Several studies suggest that the principal factor determining the flow field is vessel geometry but vessel elasticity and the non-Newtonian nature of blood can affect the details of the flow.

There is an appreciable risk of loss of patency of stents at later times, principally due to intimal hyperplasia. Stenting is associated with acute mechanical injury to the intima/media. There would not appear to have been detailed work on the role of fluid dynamics in the occurrence of intimal hyperplasia at sites of stenting, or on the preferred sites of occurrence of the process. However, histopathological cross-sections of stented vessels show in some instances a non-axisymmetric distribution of intimal hyperplasia, consistent with a role of the local flowfield in its development.

The Reynolds number for flow in large and medium-sized human arteries is typically much greater than unity, implying that inertial forces dominate over viscous forces. As a result and as implied above, the flowfield is substantially determined by the local geometry. We have recently proposed that the curvature and branching of arteries is commonly non-planar. We have proposed furthermore that the flow is commonly swirling in nature and, unlike that associated with planar curvature and branching, characterised by a relatively uniform distribution of wall shear.

In the light of these proposals and that intimal hyperplasia at end-to-end arterial bypass grafts affects preferentially regions which experience flow wall shear, we have studied the velocity field in model planar and non-planar end-to side grafts, using steady laminar flow and methods including flow visualization, MRI and computational fluid dynamics. The outstanding findings were much improved mixing within the non-planar model at the 'heel", 'floor' and 'toe,' the preferred sites for intimal hyperplasia. In addition, we found with the non-planar model a marked reduction of peak wall shear stress at the 'floor', of the anastomosis and a greatly increased flux of velocity into the occluded region proximal to the anastomosis. Consequently, wall shear stress in the occluded region was higher with the non-planar model than the planar model.

In recent model studies, we have used a physiological non-steady flow and obtained generally similar results. Moreover, in other recent studies with a model incorporating a sharp bend, we have found non-planar geometry apparently to affect the location and extent of flow separation and markedly to reduce the unsteadiness of the flow.

MR Imaging of Stents In Vitro: Preliminary in vitro MRI studies can be extended, in order to establish the accuracy of imaging the geometry and flowfield in a small series of nitinol stents of different diameter, in the range 8 mm-3 mm.

The flows will be laminar and either steady or non-steady in the physiological range; it is preferred to use a pump capable of generating physiological flow waveforms. the tubes in which the stents will be deployed will curve in one or more planes. The latter curvature will test the ability to measure stent geometry and the flowfield under nearly physiological conditions.

Although nitinol stents are metallic, their magnetic susceptibility is sufficiently close to that of human tissue to permit high quality MR imaging. Imaging strategies can be investigated which minimize artifacts. These strategies preferably include ultra-short echo times and modified spin-echo methods. Changes to the construction of the stent can also be investigated to create a stent which has both improved flow characteristics and MR imaging characteristics.

MRI Imaging of Stents in Excised Arteries: Nitinol stents supplied in freshly excised pig arteries can be used. Vasomotor activity may be lost in the preparations, but it is unlikely that their distensibility will be grossly abnormal; similar preparations are widely used in vascular distensibility studies.

The stents are preferably deployed for testing at a few selected sites where non-planar geometry can be expected— probably the origins of the coeliac, renal and common iliac arteries. To ensure near-physiological anatomy and mechanics, the stents can be deployed in vessels still tethered by surrounding tissues and still supported by major structures such as the lumbar spine.

It is possible to prepare vascular casts and study the geometry and flowfield by MRI. Vessel geometry can be determined by preparing epoxy resin casts at physiological transmural pressure; in a few instances casts in different pig preparations will be made at systolic and diastolic pressure, to determine static strain over the pulse pressure. After setting, the cast will be dissected from tissue and imaged in a small-bore MR scanner.

Figure 8:
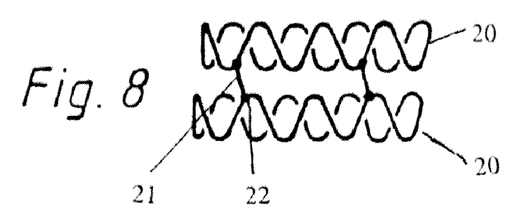
FIG. 8 shows an alternative embodiment of a stent according to the present invention.

Current designs of stents are shown in FIG. 8. A series of rings 20 are provided in which the material has the form of a vase as the ring 20 is harnessed in the azimuthal direction, with occasional link members 21 (see FIG. 9) which join one ring 20 to the next or simple spot welds 22.

Figure 9:
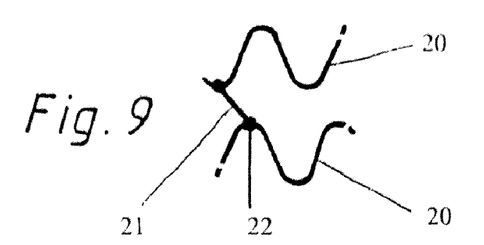
FIG. 9 shows a link member of the stent of FIG. 8.

To incorporate torsional and bending flexibility these link members 21 are replaced by elements with a considerably greater flexibility.

Figure 10:
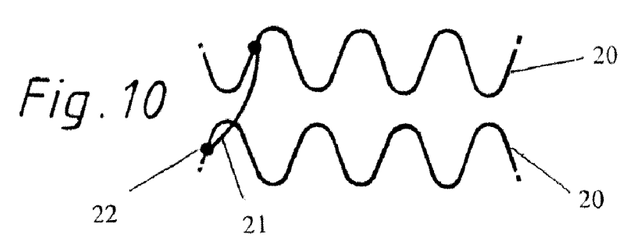
FIG. 10 shows the stent of FIG. 8 having an alternative embodiment of a link member.

The flexibility may be achieved by increasing the length of the link member 21 whilst changing their point of attachment as in FIG. 10.

Alternatively, the link members 21 may be made of an appropriate spring like shape.

Figure 11:
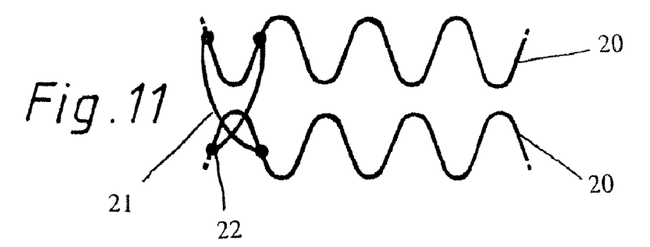
FIG. 11 shows the stent of FIG. 8 with another alternative embodiment of a link member.

In the embodiments of FIGS. 10 and 11, the link member 21 is welded at some distance away from closest point, and is more flexible by virtue of increased length.

Figure 12:
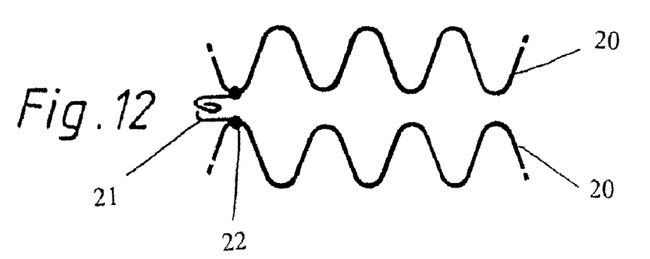
FIG. 12 shows the stent of FIG. 8 with still another alternative embodiment of a link member.

In the embodiment of FIG. 12, the link member 21 is a wavy or spring coil form (at least in part) so that it has greater flexibility.

The invention claimed is:
1. A method of imposing a shape on an intact blood vessel other than a graft, comprising inserting a stent in the vessel, the stent including a supporting portion which internally sup- ports an interior wall of the vessel, wherein the supporting portion comprises a hollow tube, the walls of which have openings therein so that the interior wall of the vessel is exposed via said openings to fluid flow along the vessel, and wherein the central axis of the hollow tube forms a non-planar, three-dimensional, at least partially helical shape and the hollow tube imposes said three-dimensional, at least partially helical shape on the central axis of the vessel, whereby swirling fluid flow is induced within the stent supported part of the vessel.

2. A method as claimed in claim 1, wherein the stent is in the form of an open lattice generally tubular framework with discrete openings at each end thereof.

3. A method as claimed in claim 1, wherein the stent is fabricated from a linked mesh so as to be at least partly helical.

4. A method as claimed in claim 1, wherein the stent is fabricated from a series of linked wire members so as to be at least partly helical.

5. A method as claimed in claim 1, wherein the stent is in the form of a series of curved rings joined together.

6. A method as claimed in claim 5, wherein the curved rings are joined together by link members.

7. A method as claimed in claim 6, wherein the link members have a wavy form.

8. A method as claimed in claim 5, wherein the curved rings are joined together by spot welds.

9. A method as claimed in claim 1, wherein the stent is fabricated from a shape memory alloy.

10. A method as claimed in claim 1, wherein the rigidity of the stent is reduced at an end thereof.

11. A method as claimed in claim 1, further comprising monitoring the condition of the vessel on which said at least partially helical shape is imposed.

12. A method as claimed in claim 11, further comprising sensing one or more internal flow conditions of the vessel.

13. A method as claimed in claim 12, further comprising transmitting a signal responsive to said one or more internal flow conditions of the vessel.

14. A method of imposing a shape on an intact blood vessel other than a graft, comprising:
providing a stent including a supporting portion, wherein the supporting portion comprises a hollow tube, the walls of which have openings therein, and wherein the central axis of the hollow tube forms a non-planar three-dimensional at least partially helical shape;
inserting the stent into the intact blood vessel;
internally supporting an interior wall of the blood vessel with the stent;
exposing the interior wall of the blood vessel to fluid flow along the vessel via the openings in the stent;
imposing the three-dimensional at least partially helical shape of the stent on a central axis of the vessel; and
inducing a swirling fluid flow within the stent supported part of the vessel.

15. The method of claim 14 further comprising monitoring a condition of the vessel on which the partially helical shape is imposed.

16. The method of claim 15 further comprising sensing one or more internal flow conditions of the vessel.

17. The method of claim 16 further comprising transmitting a signal responsive to the one or more internal flow conditions of the vessel.

18. A method of inserting a stent having a supporting portion into an associated intact vessel, comprising the step of placing the stent within the associated intact vessel such that part of the associated intact vessel is disposed around the supporting portion, and so that the stent internally supports the associated vessel part, wherein the supporting portion of the stent is of a shape and/or orientation which imposes a non-planar curve on the associated vessel whereby fluid flow within the stent supported part of the associated vessel follows a non-planar curve to induce swirl flow.

* * * * *